United States Patent
Hayashi

(10) Patent No.: US 8,405,049 B2
(45) Date of Patent: Mar. 26, 2013

(54) FLUORESCENCE DETECTION METHOD, FLUORESCENCE DETECTING DEVICE AND PROGRAM

(75) Inventor: Hironori Hayashi, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 0 days.

(21) Appl. No.: 13/148,587

(22) PCT Filed: Feb. 4, 2010

(86) PCT No.: PCT/JP2010/000686
§ 371 (c)(1),
(2), (4) Date: Aug. 9, 2011

(87) PCT Pub. No.: WO2010/095386
PCT Pub. Date: Aug. 26, 2010

(65) Prior Publication Data
US 2011/0309266 A1 Dec. 22, 2011

(30) Foreign Application Priority Data
Feb. 17, 2009 (JP) ................. 2009-033992

(51) Int. Cl.
*G01N 21/64* (2006.01)
(52) U.S. Cl. .................. 250/459.1; 250/458.1
(58) Field of Classification Search ............. 250/459.1
See application file for complete search history.

(56) References Cited

U.S. PATENT DOCUMENTS

2007/0197894 A1* 8/2007 Jo et al. .......... 600/407
2007/0267565 A1 11/2007 Nishizawa et al.
2009/0012721 A1 1/2009 Kimura et al.

FOREIGN PATENT DOCUMENTS

| JP | 02-50513 B2 | 11/1990 |
| JP | 2000-304697 A | 11/2000 |
| JP | 2005-019537 A | 1/2005 |
| JP | 2006-226698 A | 8/2006 |
| JP | 2007-127415 A | 5/2007 |

OTHER PUBLICATIONS

Iwata et al.; Photon-Counting Phase-modulation Fluorometer; Optical Review; Oct. 2001; vol. 8/No. 5, pp. 326-330.

* cited by examiner

*Primary Examiner* — Marcus Taningco
(74) *Attorney, Agent, or Firm* — Global IP Counselors, LLP

(57) ABSTRACT

Disclosed herein is a fluorescence detection method. The fluorescence detection method includes the steps of: irradiating a measurement object with laser light modulated at a predetermined frequency; receiving fluorescence emitted by the measurement object and outputting two or more pulsed fluorescent signals; setting reference timing in units of period corresponding to the frequency; acquiring a generation time to output of each of the pulsed fluorescent signals based on the reference timing; generating a cumulative fluorescent signal indicating the relationship between a generation frequency of the pulsed fluorescent signal and the generation time; determining, by using a signal corresponding to modulation of the laser light as a reference signal, a phase difference between the reference signal and the cumulative fluorescent signal; and determining, by using the phase difference, a fluorescence relaxation time of the fluorescence emitted by the measurement object.

11 Claims, 8 Drawing Sheets

FLUORESCENCE DETECTION METHOD, FLUORESCENCE DETECTING DEVICE AND PROGRAM

TECHNICAL FIELD

The present invention relates to a method and a device for detecting fluorescence by receiving fluorescence emitted by a measurement object irradiated with laser light and processing a fluorescent signal obtained at this time. The present invention also relates to a program for causing a computer to perform processing of two or more pulsed fluorescent signals obtained as a light-receiving signal of fluorescence emitted by a measurement object irradiated with laser light modulated at a predetermined frequency.

Particularly, the present invention relates to a fluorescence detection device to be applied to an analyzing device, such as a flow cytometer for use in medical and biological fields, which identifies and analyzes a measurement object such as cells, DNA, or RNA by using fluorescence emitted by a fluorochrome.

BACKGROUND ART

A flow cytometer for use in medical and biological fields includes a fluorescence detection device that receives fluorescence emitted by a fluorochrome of a measurement object irradiated with laser light and identifies the kind of the measurement object.

More specifically, in the flow cytometer, a suspension liquid containing a measurement object such as a biological material (e.g., cells, DNA, RNA, enzymes, or proteins) labeled with a fluorescent reagent is allowed to flow through a tube together with a sheath liquid flowing under pressure at a speed of about 10 m/sec or less to form a laminar sheath flow. The flow cytometer receives fluorescence emitted by a fluorochrome attached to the measurement object by irradiating the measurement object in the laminar sheath flow with laser light and identifies the measurement object by using the fluorescence as a label.

The flow cytometer can measure, for example, the relative amounts of DNA, RNA, enzymes, proteins, etc. contained in a cell and can quickly analyze their functions. Further, a cell sorter or the like is used to identify a specific type of cell or chromosome based on fluorescence and selectively and quickly collect only the identified cells or chromosomes alive.

For example, in order to analyze a biological material such as DNA by a flow cytometer, a fluorochrome is previously attached to the biological material by a fluorescent reagent. The biological material is labeled with a fluorochrome different from a fluorochrome attached to a microbead (which will be described later) and is mixed with a liquid containing microbeads having a diameter of 5 to 20 μM and a specific structure such as a carboxyl group provided on the surface thereof. The structure such as a carboxyl group acts on and is coupled to a biological material having a certain known structure. Therefore, simultaneous detection of fluorescence emitted by the microbead and fluorescence emitted by the biological material indicates that the biological material has been coupled to the structure provided on the surface of the microbead. This makes it possible to analyze the characteristics of the biological material. In order to quickly analyze the characteristics of a biological material by using various microbeads having different structures for coupling, very many kinds of fluorochromes are required.

Patent Document 1 describes that a fluorescence relaxation time of fluorescence emitted by irradiating a measurement object such as a microbead with laser light whose intensity is modulated at a predetermined frequency is determined. The fluorescence relaxation time varies depending on the type of fluorochrome used, and therefore the type of the fluorescence can be identified using the fluorescence relaxation tine and the type of the measurement object can be identified by identifying the type of the fluorescence.

PRIOR ART DOCUMENT

Patent Document

Patent Document 1: Japanese Patent Application Laid-Open No. 2006-226698

DISCLOSURE OF THE INVENTION

Problems to be Solved by the Invention

According to Patent Document 1, it is possible to efficiently and quickly identify fluorescence based on a fluorescence relaxation time, but the measurement accuracy of a fluorescence relaxation time is not always high. For example, when received fluorescence is weak and therefore a light-receiving signal is composed of two or more discrete pulsed fluorescent signals, a phase difference required to determine a fluorescence relaxation time cannot be determined.

In order to solve the above problem, it is an object of the present invention to provide a fluorescence detection method, a fluorescence detection device, and a program therefor which make it possible to determine a fluorescence relaxation time with high accuracy even when fluorescence is weak and a light-receiving signal thereof is composed of two or more discrete pulsed fluorescent signals.

Means for Solving the Problems

A method of the present invention for detecting fluorescence by receiving fluorescence emitted by a measurement object irradiated with laser light and processing a fluorescent signal obtained at this time, the method comprising the steps of: irradiating the measurement object with laser light modulated at a predetermined frequency; receiving fluorescence emitted by the measurement object and outputting two or more pulsed fluorescent signals; setting reference timing in units of period corresponding to the frequency; acquiring a generation time to output of each of the pulsed fluorescent signals based on the reference timing; generating a cumulative fluorescent signal indicating a relationship between a generation frequency of the pulsed fluorescent signal and the generation time; determining, by using a signal corresponding to modulation of the laser light as a reference signal, a phase difference between the reference signal and the cumulative fluorescent signal; and determining, by using the phase difference, a fluorescence relaxation time of the fluorescence emitted by the measurement object.

A device of the present invention for detecting fluorescence by receiving fluorescence emitted by a measurement object irradiated with laser light and processing a fluorescent signal obtained at this time, the device comprising: a laser light source unit that irradiates a measurement object with laser light modulated at a predetermined frequency; a light-receiving unit that receives fluorescence emitted by the measurement object and outputs two or more pulsed fluorescent signals; and a processing unit that determines, by using the fluorescent signals output by the light-receiving unit by irradiation of the measurement object with the laser light, a fluorescence relaxation time of the fluorescence emitted by the measurement object, wherein the processing unit comprises: a reference timing setting unit that sets reference timing in units of period corresponding to the frequency; a pulse generation time acquisition unit that acquires a generation time to output of each of the pulsed fluorescent signals based on the reference timing; a cumulative fluorescent signal generation unit that generates a cumulative fluorescent signal indicating a relationship between a generation frequency of the pulsed fluorescent signal and the pulse generation time; a phase difference acquisition unit that determines, by using a signal corresponding to modulation of the laser light as a reference signal, a phase difference between the reference signal and the cumulative fluorescent signal; and a fluorescence relaxation time acquisition unit that determines, by using the phase difference determined by the phase difference acquisition unit, a fluorescence relaxation time of the fluorescence emitted by the measurement object.

A program of the present invention for causing a computer to execute processing of two or more pulsed fluorescent signals obtained as a light-receiving signal of fluorescence emitted by a measurement object irradiated with laser light modulated at a predetermined frequency, the computer executing the steps of: setting reference timing in units of period corresponding to the frequency; acquiring a generation time to output of each of the pulsed fluorescent signals based on the reference timing; generating a cumulative fluorescent signal indicating a relationship between a generation frequency of the pulsed fluorescent signal and the generation time; determining, by using a signal corresponding to modulation of the laser light as a reference signal, a phase difference between the reference signal and the cumulative fluorescent signal; and determining, by using the phase difference, a fluorescence relaxation time of the fluorescence emitted by the measurement object.

Effects of the Invention

According to the present invention, it is possible to determine a fluorescence relaxation time with high accuracy.

EMBODIMENTS FOR CARRYING OUT THE INVENTION

Hereinbelow, a flow cytometer appropriately using a fluorescence detection device according to the present invention will be described in detail based on the following embodiments.

<First Embodiment>
(Overall Structure of Flow Cytometer)

Figure 1:
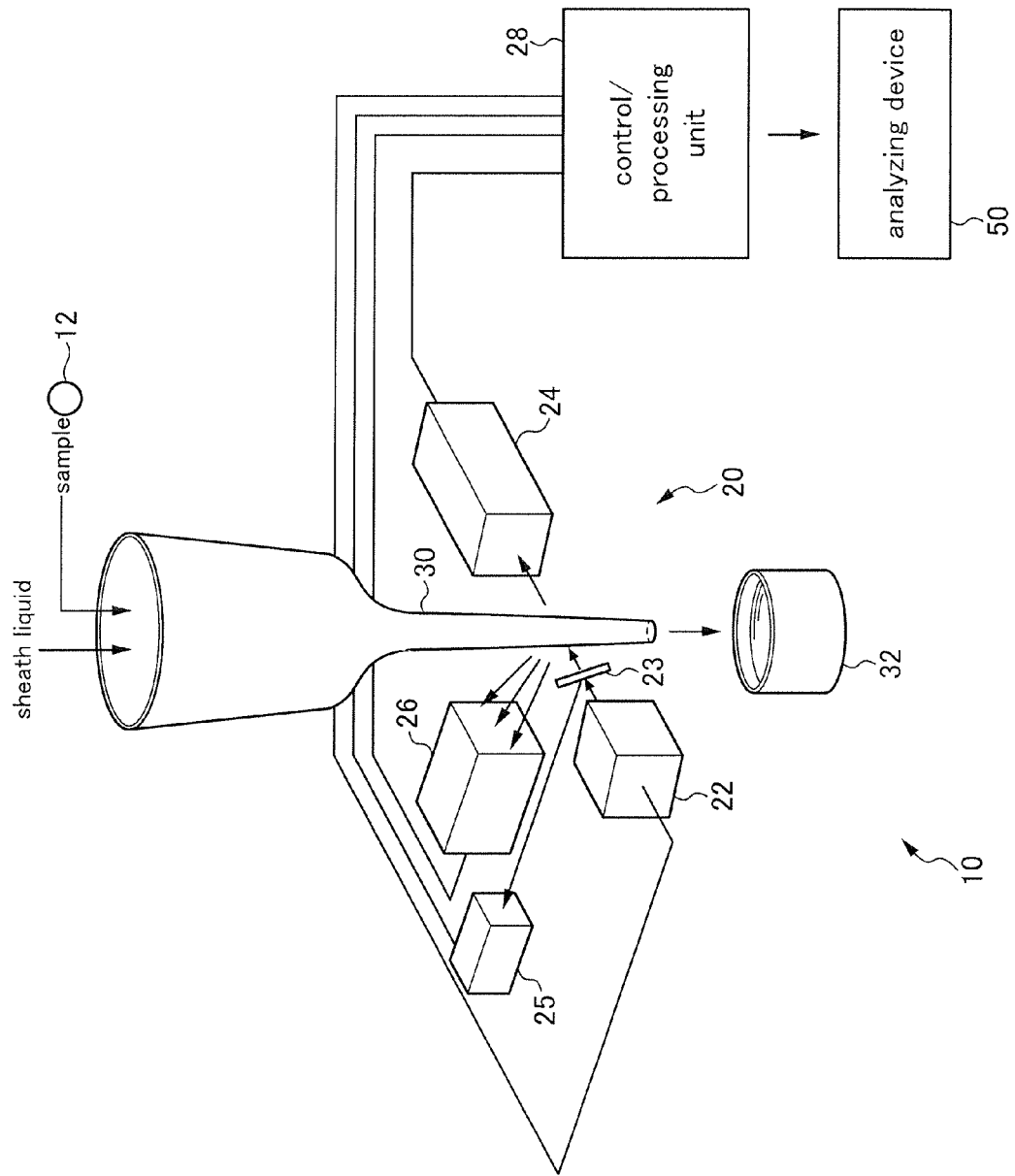
FIG. 1 is a schematic diagram illustrating the structure of a flow cytometer according to one embodiment of a fluorescence detection device of the present invention.

The overall structure of a flow cytometer according to a first embodiment will be described first with reference to FIG. 1. FIG. 1 is a schematic diagram illustrating the structure of a flow cytometer 10 using the fluorescence detection device according to the present invention.

The flow cytometer 10 includes a signal processing device 20 and an analyzing device 50. The signal processing device 20 detects and processes a fluorescent signal of fluorescence emitted by a fluorochrome in a sample 12 such as a microbead or a cell by irradiating the sample 12 with laser light. The analyzing device 50 analyzes a measurement object in the sample 12 from processing results obtained by the signal processing device 20.

The signal processing device 20 includes a laser light source unit 22, light-receiving units 24, 25, and 26, a control/processing unit 28, and a tube 30. The control/processing unit 28 includes a light source control unit 40 (see FIG. 2) and an A/D converter 46 (see FIG. 2). The light source control unit 40 modulates the intensity of laser light emitted from the laser light source unit 22. The A/D converter 46 performs A/D conversion on a fluorescent signal from the sample 12. The tube 30 allows the sample 12 to flow therethrough together with a sheath liquid forming a high-speed flow so that a laminar sheath flow is formed. The laminar sheath flow has a diameter of for example, 100 μm and a flow rate of 1 to 10 msec. When a microbead is used as the sample 12, the diameter of the microbead is several micrometers to 30 μm. A collection vessel 32 is provided under the outlet of the tube 30.

The laser light source unit 22 is a unit that emits laser light whose intensity is modulated at a predetermined frequency. A lens system is provided so that laser light is focused on a predetermined position in the tube 30. The focus position is defined as a measurement point at which the sample 12 is measured.

(Laser Light Source Unit)

The laser light source unit 22 emits CW (continuous-wave) laser light of constant intensity while modulating the intensity of the CW laser light. Laser light emitted from the laser light source unit 22 is focused by the lens system (not illustrated) on the measurement point in the tube 30.

A light source that emits laser light is, for example, a semiconductor laser. The laser light has an output of, for example, about 5 to 100 mW and a wavelength of, for example, 350 nm to 800 nm.

The laser light source unit 22 is connected to the control/processing unit 28. The control/processing unit 28 supplies a modulation signal modulated at a predetermined frequency to the laser light source unit 22 to modulate the intensity of laser light.

The fluorochrome to be excited by laser light is attached to the sample 12 such as a biological material or microbead to be measured. The sample 12 is irradiated with laser light at the measurement point and emits fluorescence in several to several tens of microseconds during which the sample 12 passes through the measurement point on which laser light is focused.

(Light-Receiving Unit)

A beam splitter 23 is provided between the laser light source unit 22 and the tube 30. Part of laser light emitted from the laser light source unit 22 passes through the beam splitter 23 and illuminates the sample 12 passing through the measurement point. Further, part of laser light emitted from the laser light source unit 22 is reflected by the beam splitter 23 and illuminates the light-receiving unit 25.

The light-receiving unit 24 is arranged so as to be opposed to the laser light source unit 22 with the tube 30 provided therebetween. Laser light that has passed through the beam splitter 23 is forward-scattered by the sample 12 passing through the measurement point. The light-receiving unit 24 is equipped with a photoelectric converter that outputs a detection signal indicating the passage of the sample 12 through the measurement point. The signal output from the light-receiving unit 24 is supplied to the control/processing unit 28, and is used in the control/processing unit 28 as a trigger signal to announce the timing of passage of the sample 12 through the measurement point in the tube 30.

The light-receiving unit 25 is arranged so as to receive part of laser light reflected by the beam splitter 23. The light-receiving unit 25 is equipped with a photoelectric converter that receives laser light reflected by the beam splitter 23 and outputs a signal of received light. The signal output from the light-receiving unit 25 is a signal corresponding to modulation of laser light, and is supplied to the control/processing unit 28. The signal supplied from the light-receiving unit 25 to the control/processing unit 28 is used as a reference signal to determine a phase difference from the fluorescent signal.

The light-receiving unit 26 is arranged in a direction perpendicular to a direction in which laser light emitted from the laser light source unit 22 travels and to a direction in which the sample 12 moves in the tube 30. The sample 12 passing through the measurement point is irradiated with laser light that has passed through the beam splitter 23. The light-receiving unit 26 is equipped with a photoelectric converter that receives fluorescence emitted by the sample 12.

The photoelectric converter converts light received by its photoelectric surface into an electrical signal (light-receiving signal). The light-receiving signal is supplied to the control/processing unit 28. For example, when fluorescence received by the light-receiving unit 26 is very weak and therefore pulsed signals each corresponding to a single photon are acquired, a light-receiving signal composed of two or more very weak pulsed fluorescent signals is output.

(Control/Processing Unit)

Figure 2:
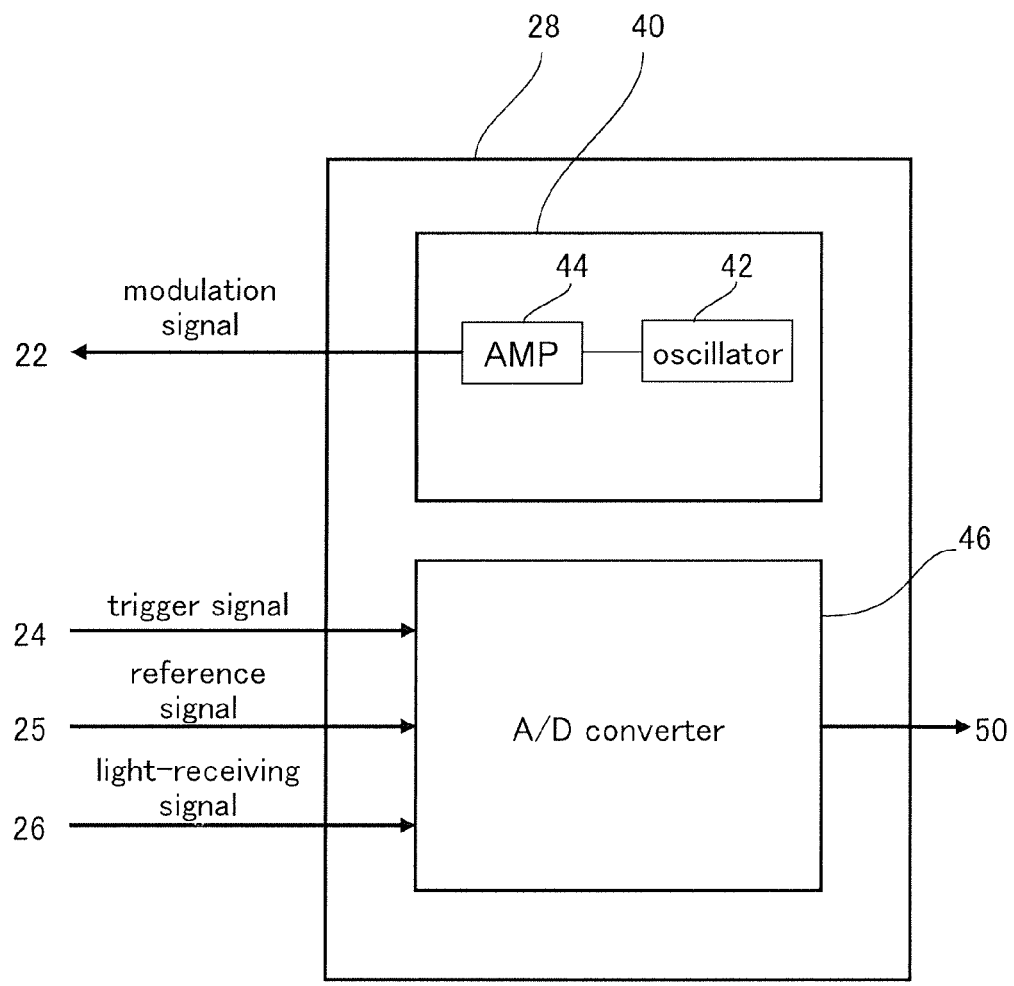
FIG. 2 is a schematic diagram illustrating the structure of one example of a control/processing unit for use in the fluorescence detection device illustrated in FIG. 1.

FIG. 2 is a schematic diagram illustrating the structure of one example of the control/processing unit 28. As described above, the control/processing unit 28 includes the light source control unit 40 and the A/D converter 46.

The light source control unit 40 includes an oscillator 42 and an amplifier 44. The light source control unit 40 generates a modulation signal for modulating the intensity of laser light and supplies the generated modulation signal to the laser light source unit 22.

The oscillator 42 outputs a sinusoidal signal of a predetermined frequency. The frequency of the sinusoidal signal is set to a value in the range of, for example, 1 to 50 MHz. The sinusoidal signal of a predetermined frequency output from the oscillator 42 is amplified by the amplifier 44 and is supplied to the laser light source unit 22.

The A/D converter 46 performs A/D conversion on the light-receiving signal output from the light-receiving unit 26 and the reference signal supplied from the light-receiving unit 25. The A/D conversion is started based on the trigger signal supplied from the light-receiving unit 24. As the A/D converter 46, one that performs sampling at several gigahertz is used. As will be described below, this makes it possible to, when fluorescence is weak, obtain a light-receiving signal composed of discrete pulsed fluorescent signals. The A/D converted light-receiving signal is supplied to the analyzing device 50.

(Analyzing Device)

Figure 3:
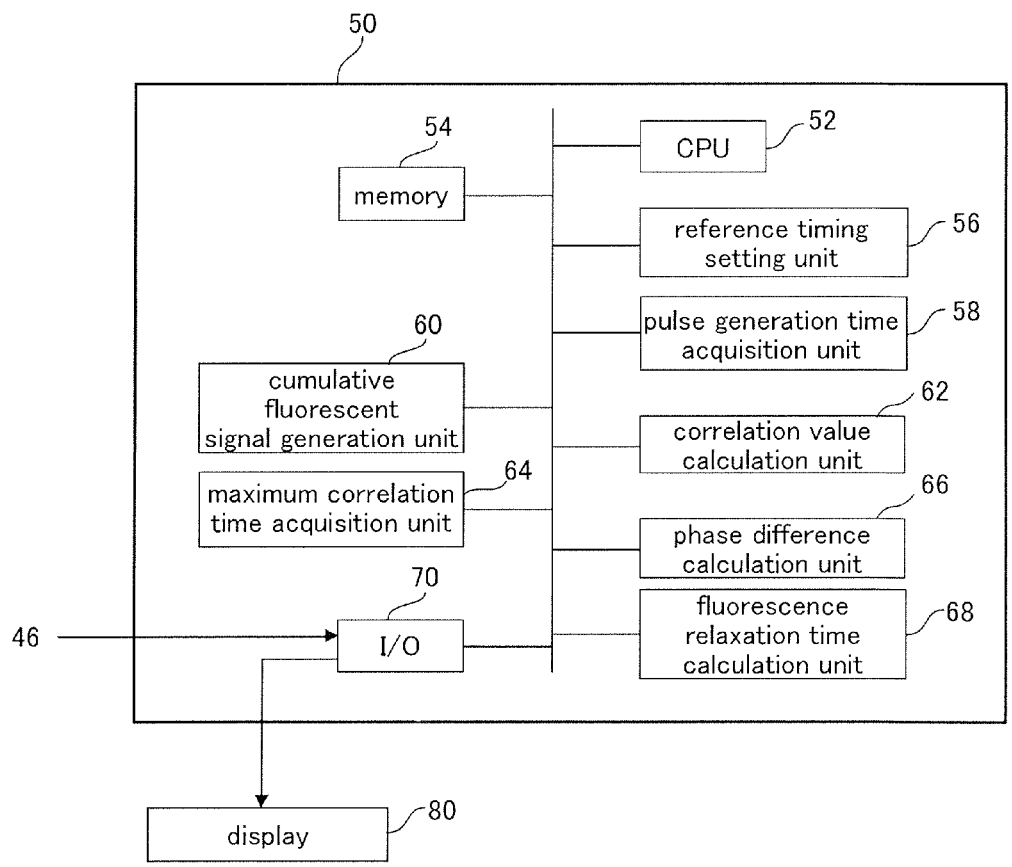
FIG. 3 is a schematic diagram illustrating the structure of one example of an analyzing device for use in the fluorescence detection device illustrated in FIG. 1.

FIG. 3 is a schematic diagram illustrating the structure of one example of the analyzing device 50. The analyzing device 50 is a device provided by executing a predetermined program on a computer. The analyzing device 50 includes a CPU 52, a memory 54, and an input/output port 70, and further includes a reference timing setting unit 56, a pulse generation time acquisition unit 58, a cumulative fluorescent signal generation unit 60, a correlation value calculation unit 62, a maximum correlation time acquisition unit 64, a phase difference calculation unit 66, and a fluorescence relaxation time calculation unit 68. The analyzing device 50 is connected to a display 80.

The CPU 52 is an arithmetic processor provided in the computer to virtually make various calculations of the reference timing setting unit 56, the pulse generation time acquisition unit 58, the cumulative fluorescent signal generation unit 60, the correlation value calculation unit 62, the maximum correlation time acquisition unit 64, the phase difference calculation unit 66, and the fluorescence relaxation time calculation unit 68.

The memory 54 includes a hard disk or ROM that stores a program to be executed on the computer to provide the reference timing setting unit 56, the pulse generation time acquisition unit 58, the cumulative fluorescent signal generation unit 60, the correlation value calculation unit 62, the maximum correlation time acquisition unit 64, the phase difference calculation unit 66, and the fluorescence relaxation time calculation unit 68 and a RAM that stores processing results calculated by these units and signals supplied from the input/output port 70. The memory 54 continuously stores the light-receiving signal and the reference signal supplied from the A/D converter 46.

The input/output port 70 is used to receive the reference signal and the light-receiving signal supplied from the A/D converter 46 and to output information about the processing results generated by the units to the display 80. The display 80 displays the values of the processing results determined by the units such as a pulse generation time, a cumulative fluorescent signal, a correlation value, a maximum correlation time, a phase difference, and a fluorescence relaxation time.

Figure 4A:
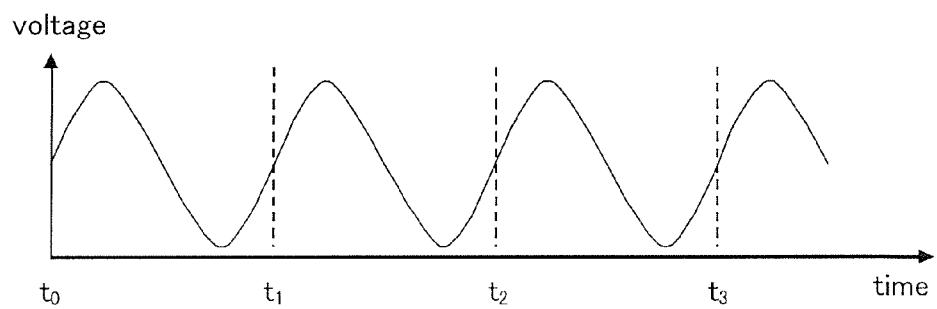
FIGS. 4(a) and 4(b) are graphs each illustrating one example of a signal stored in a memory of the analyzing device illustrated in FIG. 1.
Figure 4B:
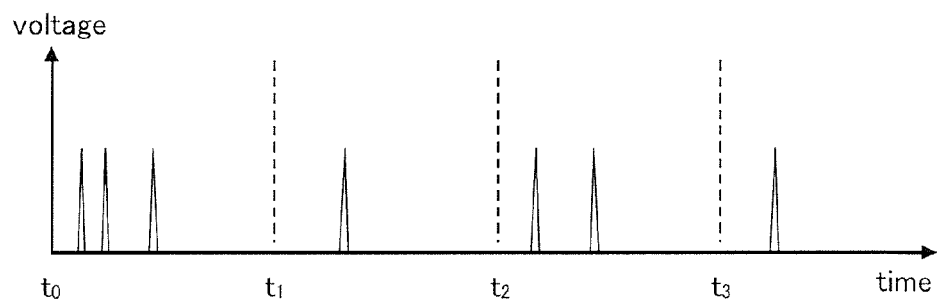

FIGS. 4(a) and 4(b) are graphs each illustrating one example of the signal stored in the memory 54 of the analyzing device. FIG. 4(a) is a graph illustrating one example of the reference signal supplied from the light-receiving unit 25 to the A/D converter 46 and stored in the memory 54. FIG. 4(b) is a graph illustrating one example of the light-receiving signal supplied from the light-receiving unit 26 to the A/D converter 46 and stored in the memory 54. When the light-receiving unit 26 receives such weak light that a pulsed fluorescent signal is acquired every time one photon is received, as illustrated in FIG. 4(b), each individual fluorescent signal is measured as a pulsed electrical signal.

The reference timing setting unit 56 sets reference timing ($t_i$: i is an integer) at a constant time interval for the light-receiving signal and the reference signal stored in the memory 54. The time interval is set to a period corresponding to a frequency at which laser light is modulated. For example, when laser light is modulated at a frequency of 10 MHz, the time interval is set to 100 nsec that is a period corresponding to 10 MHz. The signals illustrated in FIGS. 4(a) and 4(b) are examples in which the reference timing is set per period (one cycle) corresponding to a frequency at which laser light is modulated, but the reference timing may be set per unit such as per two cycles or three cycles.

The pulse generation time acquisition unit 58 acquires, based on the reference timing ti, a pulse generation time that is the time to output of each pulsed fluorescent signal. In the case of the example illustrated in FIG. 4(b), three pulsed fluorescent signals are measured between the reference timing t0 and the reference timing t1. The pulse generation time acquisition unit 58 acquires the time (generation time) from the reference timing t0 to generation of each of the three pulsed fluorescent signals. Between the reference timing t1 and the reference timing t2, one pulsed fluorescent signal is measured. The pulse generation time acquisition unit 58 acquires the time (generation time) from the reference timing t1 to generation of the fluorescent signal. In this way, the pulse generation time acquisition unit 58 acquires the time (generation time) from the reference timing t1 to output of each pulsed fluorescent signal.

The time (generation time) to generation of a pulsed fluorescent signal is acquired as the time in the middle between the time when a pulsed electrical signal exceeds a predetermined threshold value and the time when the pulsed electrical signal falls below the threshold value. The threshold value is set to prevent a noise component from being acquired by mistake as a pulsed fluorescent signal.

Figure 5A:
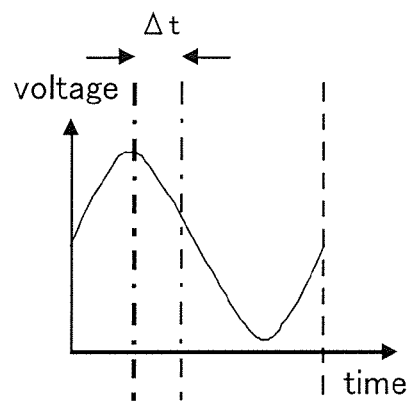
FIG. 5(a) is a graph illustrating one example of a reference signal obtained by the fluorescence detection device illustrated in FIG. 1.
Figure 5B:
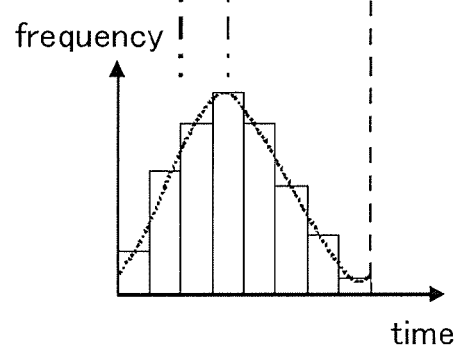
FIG. 5(b) is a graph illustrating one example of a signal acquired by a cumulative fluorescent signal generation unit of the analyzing device illustrated in FIG. 3.

The cumulative fluorescent signal generation unit 60 determines a cumulative fluorescent signal that indicates the relationship between the pulse generation time determined by the pulse generation time acquisition unit 58 and the frequency of output of a pulsed fluorescent signal at the pulse generation time. FIG. 5(b) is a graph illustrating one example of the cumulative fluorescent signal acquired by the cumulative fluorescent signal generation unit 60 of the analyzing device 50. The cumulative fluorescent signal generation unit 60 divides the pulse generation time determined by the pulse generation time acquisition unit 58 into two or more time zones and calculates the frequency of generation of a pulse per time zone.

Further, the cumulative fluorescent signal generation unit 60 generates, when the time of the reference timing is set to time 0, a cumulative fluorescent signal obtained by representing, as a signal value, the frequency of generation of a pulsed fluorescent signal at the time in the middle of the time zone. For example, the cumulative fluorescent signal is a signal represented by a histogram illustrated in FIG. 5(b). It should be understood that it is possible to generate a cumulative fluorescent signal represented by a histogram in which the difference in height between adjacent bars is smaller by setting the width of the time zones to a smaller value. However, in this case, the parameter of a fluorescent signal to be cumulated is small, and therefore noise is likely to be generated. For this reason, it is preferred that the setting of width of the time zones is previously searched and determined so that a continuous and smooth cumulative fluorescent signal can be generated.

Figure 5C:
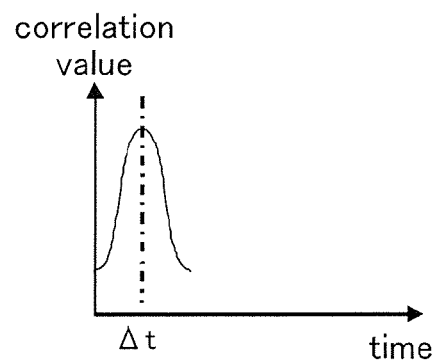
FIG. 5(c) is a graph illustrating one example of a signal acquired by a correlation value calculation unit of the analyzing device.

The correlation value calculation unit 62 determines a correlation value between the cumulative fluorescent signal determined by the cumulative fluorescent signal generation unit 60 and the reference signal. The reference signal used to calculate a correlation value is a signal during one cycle divided by the reference timing. Such a signal during one cycle may be obtained by averaging a stored reference signal or by selecting one reference signal during one cycle as a representative. FIG. 5(a) is a graph illustrating one example of the reference signal during one cycle. The correlation value calculation unit 62 acquires a correlation value between the reference signal and the cumulative fluorescent signal by shifting the reference signal in the direction of time. FIG. 5(c) is a graph illustrating one example of a signal of the correlation value acquired by the correlation value calculation unit 62 of the analyzing device 50, wherein the horizontal axis represents the time during which the reference signal is shifted in the direction of time and the vertical axis represents the correlation value.

The maximum correlation time acquisition unit 64 determines the time $\Delta t$ (maximum correlation time) when the correlation value determined by the correlation value calculation unit 62 is maximized.

The phase difference calculation unit 66 determines a phase difference between the reference signal and the cumulative fluorescent signal by using the maximum correlation time $\Delta t$ determined by the maximum correlation time acquisition unit 64. The phase difference $\theta$ is determined by $\theta = 2\pi f \Delta t$ where f is the frequency of the modulation signal for modulating laser light.

The fluorescence relaxation time calculation unit 68 determines a fluorescence relaxation time $\tau$ of the fluorescence emitted by the measurement object by using the phase difference $\theta$ determined by the phase difference calculation unit 66. The fluorescence relaxation time $\tau$ is determined by $\tau = \tan \theta / (2\pi f)$.

Figure 6:
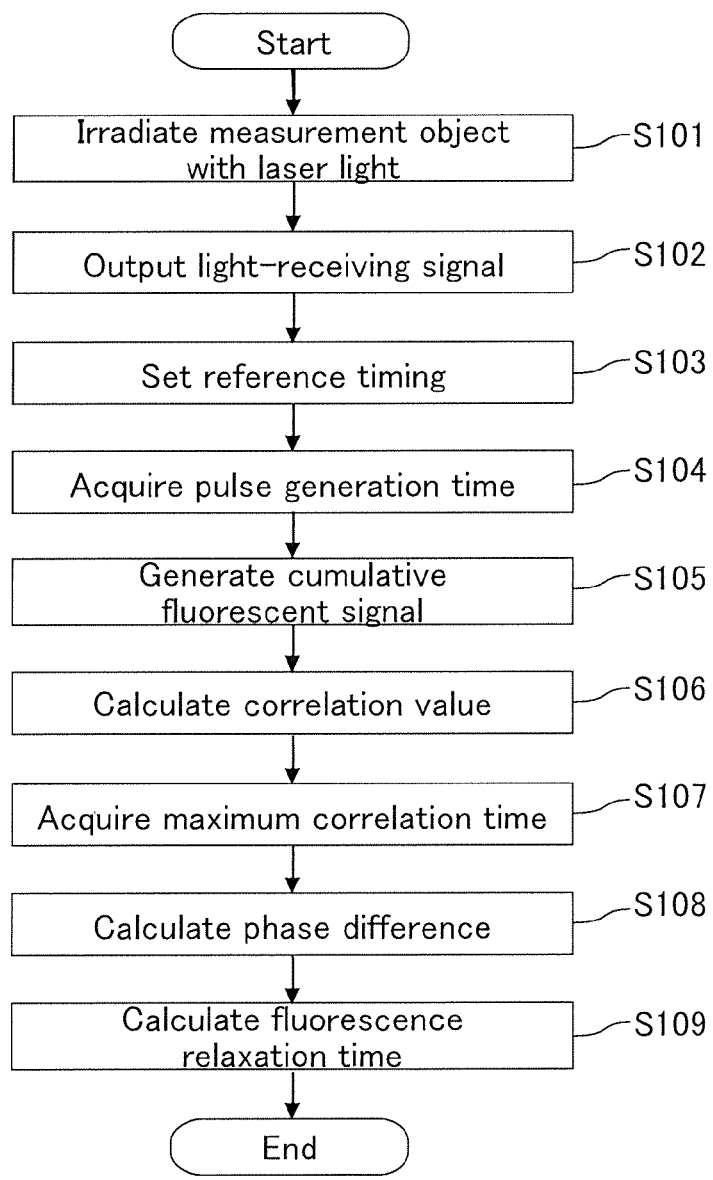
FIG. 6 is a flow chart of one embodiment of a fluorescence detection method according to the present invention.

Hereinbelow, a fluorescence detection method according to this embodiment will be described with reference to FIG. 6. FIG. 6 is a flow chart of the fluorescence detection method according to this embodiment.

According to the fluorescence detection method of this embodiment, first, the laser light source unit 22 irradiates a measurement object with laser light modulated at a predetermined frequency (S101). Then, the light-receiving unit 26 receives fluorescence emitted by the measurement object and outputs a light-receiving signal including two or more pulsed fluorescent signals (S102).

Then, the reference timing setting unit 56 sets reference timing in units of period corresponding to the frequency (S103). Then, the pulse generation time acquisition unit 58 acquires, based on the reference timing, a generation time to output of each of the pulsed fluorescent signals (S104). Then, the cumulative fluorescent signal generation unit 60 generates a cumulative fluorescent signal indicating the relationship between the generation frequency of the pulsed fluorescent signal and the generation time (S105). Then, the correlation value calculation unit 62 determines a correlation value between the cumulative fluorescent signal and a reference signal (S106). Then, the maximum correlation time acquisition unit 64 acquires a maximum correlation time at which the correlation value determined by the correlation value calculation unit 62 is maximized (S107). Then, the phase difference calculation unit 66 determines, by using a signal corresponding to modulation of the laser light as a reference signal, a phase difference between the cumulative fluorescent signal and the reference signal (S108). Then, the fluorescence relaxation time calculation unit 68 determines a fluorescence relaxation time of the fluorescence emitted by the measurement object by using the phase difference determined by the phase difference calculation unit 66 (S109).

A program according to this embodiment is a program for causing a computer to execute the processing of two or more pulsed fluorescent signals obtained as a light-receiving signal of fluorescence emitted by a measurement object irradiated with laser light modulated at a predetermined frequency. This program causes a computer to execute the step of setting reference timing in units of period corresponding to the frequency, the step of acquiring, based on the reference timing, a generation time to output of each of the pulsed fluorescent signals, the step of generating a cumulative fluorescent signal indicating the relationship between the generation frequency of the pulsed fluorescent signal and the generation time, the step of determining, by using a signal corresponding to modulation of the laser light as a reference signal, a phase difference between the cumulative fluorescent signal and the reference signal, and the step of determining a fluorescence relaxation time of the fluorescence emitted by the measurement object by using the phase difference. This program is stored in the memory 54 of the analyzing device 50.

According to this embodiment, even when fluorescence is weak and therefore a light-receiving signal is composed of two or more pulsed fluorescent signals, a fluorescence relaxation time can be measured with high accuracy by using a cumulative fluorescent signal.

<Second Embodiment>

As described above, in the case of the first embodiment, a signal obtained by reflecting part of laser light emitted from the laser light source unit 22 on the beam splitter 23 and receiving the reflected laser light by the light-receiving unit 25 is used as a reference signal. A second embodiment is different from the first embodiment in that the beam splitter 23 and the light-receiving unit 25 are omitted, and a modulation signal output from the light source control unit 40 is supplied to both the laser light source unit 22 and the A/D converter 46, and the modulation signal supplied from the light source control unit 40 to the A/D converter 46 is used as a reference signal. In this case, a power splitter is used in the light source control unit 40 to split the modulation signal. The other structures of the second embodiment are the same as those of the first embodiment.

According to this embodiment, even when fluorescence is weak, a fluorescence relaxation time can be measured with high accuracy by a simpler structure.

<Third Embodiment>

As described above, in the case of the first embodiment, the reference signal and the fluorescent signal supplied from the A/D converter 46 to the input/output port 70 are stored in the memory 54. A third embodiment is different from the first embodiment in that the reference signal and the fluorescent signal supplied from the A/D converter 46 to the input/output port 70 are not stored in the memory 54 but are directly subjected to subsequent signal processing.

The sinusoidal signal output by the light source control unit 40 has a predetermined frequency f. Therefore, the reference timing setting unit 56 sets reference timing in units of period corresponding to the frequency f for the reference signal and the fluorescent signal supplied to the input/output port 70.

The pulse generation time acquisition unit 58 acquires, based on the reference timing, the time (generation time) to generation of each of the pulsed fluorescent signals. Information about the generation time is stored in the memory 54.

Then, a cumulative fluorescent signal is determined using the information about the generation time in the same manner as in the first embodiment, and thereafter the same processing as the first embodiment is performed.

According to this embodiment, even when fluorescence is weak, a fluorescence relaxation time can be measured with high accuracy by a smaller memory capacity.

<Fourth Embodiment>

Figure 7:
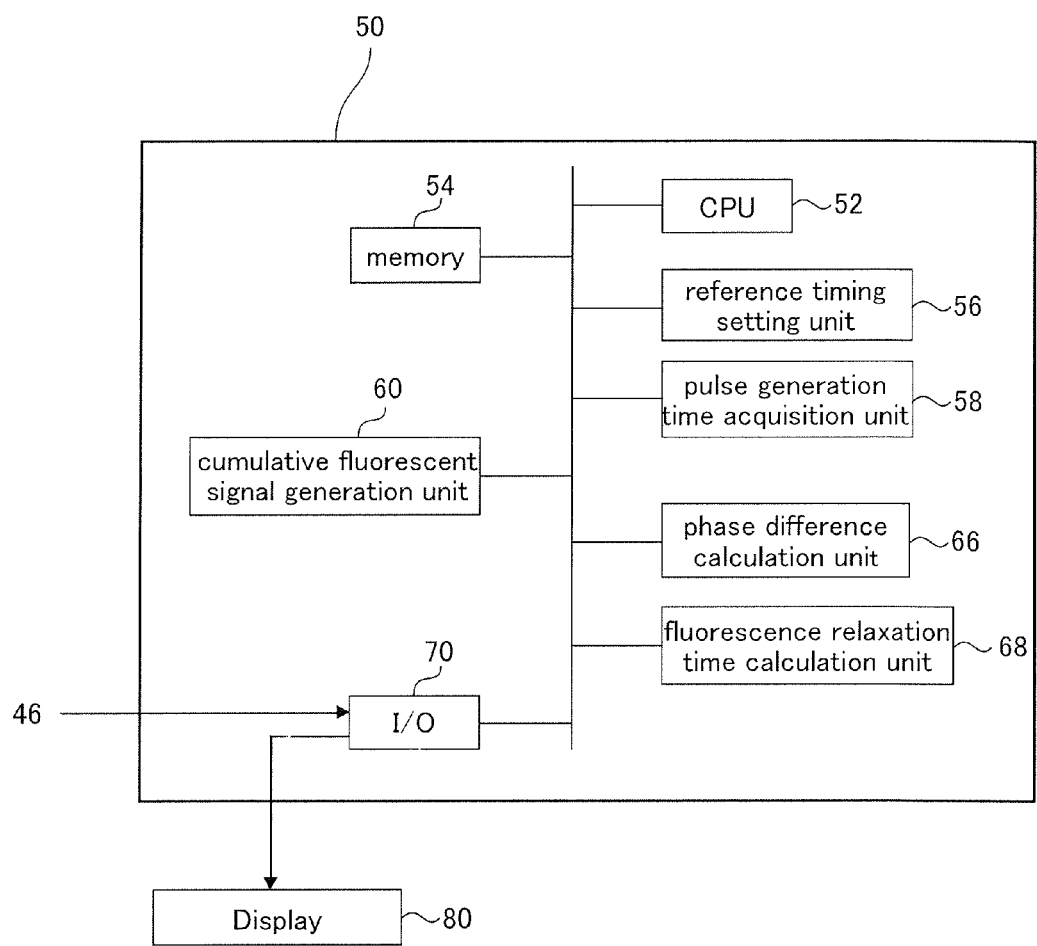
FIG. 7 is a schematic diagram illustrating the structure of another example of the analyzing device for use in the fluorescence detection device illustrated in FIG. 1.

As described above, in the case of the first embodiment, the correlation value calculation unit 62 determines a correlation value between the cumulative fluorescent signal and the reference signal by using the cumulative fluorescent signal determined by the cumulative fluorescent signal generation unit 60. A fourth embodiment is different from the first embodiment in that a correlation value between the cumulative fluorescent signal and the reference signal is not determined but a phase difference between the reference signal and the cumulative fluorescent signal is determined. FIG. 7 is a schematic diagram illustrating the structure of one example of the analyzing device 50 of this embodiment. The structure of this embodiment is the same as that of the first embodiment except that the correlation value calculation unit 62 and the maximum correlation time acquisition unit 64 provided in the first embodiment are omitted.

The cumulative fluorescent signal generation unit 60 divides the pulse generation time determined by the pulse generation time acquisition unit 58 into two or more time zones and calculates a pulse generation frequency per time zone to generate a cumulative fluorescent signal. Further, the cumulative fluorescent signal generation unit 60 of this embodiment determines a delay time of the cumulative fluorescent signal with respect to the modulation signal by performing fitting of the cumulative fluorescent signal to a signal (sinusoidal signal) having the same shape as the modulation signal for modulating laser light. The fitting is performed by, for example, the method of least squares. In FIG. 5($b$), the dotted line represents a signal obtained by fitting of the cumulative fluorescent signal.

The phase difference calculation unit 66 determines, by using the cumulative fluorescent signal determined by the cumulative fluorescent signal generation unit 60, a delay time $\Delta t$ of the cumulative fluorescent signal with respect to the modulation signal, and further determines a phase difference from the delay time $\Delta t$.

Figure 8:
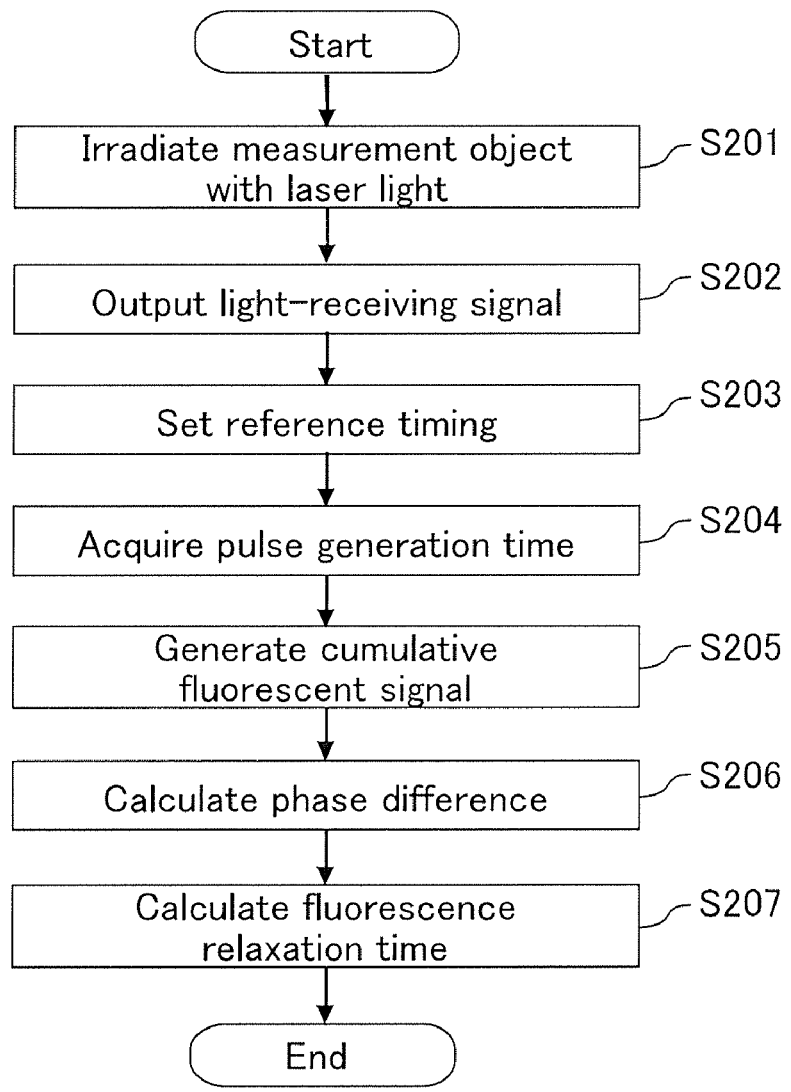
FIG. 8 is a flow chart of another embodiment of the fluorescence detection method according to the present invention.

Hereinbelow, a fluorescence detection method according to this embodiment will be described with reference to FIG. 8. FIG. 8 is a flow chart of the fluorescence detection method according to this embodiment.

According to the fluorescence detection method of this embodiment, first, the laser light source unit 22 irradiates a measurement object with laser light modulated at a predetermined frequency (S201). Then, the light-receiving unit 26 receives fluorescence emitted by the measurement object and outputs a light-receiving signal including two or more pulsed fluorescent signals (S202).

Then, the reference timing setting unit 56 sets reference timing in units of period corresponding to the frequency (S203). Then, the pulse generation time acquisition unit 58 acquires, based on the reference timing, a generation time to output of each of the pulsed fluorescent signals (S204). Then, the cumulative fluorescent signal generation unit 60 generates a cumulative fluorescent signal indicating the relationship between the generation frequency of the pulsed fluorescent signal and the generation time (S205). Then, the phase difference calculation unit 66 determines, by using a signal corresponding to modulation of the laser light as a reference signal, a phase difference between the reference signal and the cumulative fluorescent signal (S206). Then, the fluorescence relaxation time calculation unit 68 determines, by using the phase difference determined by the phase difference calculation unit 66, a fluorescence relaxation time of the fluorescence emitted by the measurement object (S207).

According to this embodiment, even when fluorescence is weak, a fluorescence relaxation time can be determined with high accuracy by a simpler structure.

DESCRIPTION OF REFERENCE NUMERALS 10 flow cytometer
12 sample
20 signal processing unit
22 laser light source unit
23 beam splitter
24, 25, 26 light-receiving units
28 control/processing unit
30 tube
32 collection vessel
40 light source control unit
42 oscillator
44 amplifier
46 A/D converter
50 analyzing device
52 CPU
54 memory
56 reference timing setting unit
58 pulse generation time acquisition unit
60 cumulative fluorescent signal generation unit
62 correlation value calculation unit
64 maximum correlation time acquisition unit
66 phase difference calculation unit
68 fluorescence relaxation time calculation unit
70 input/output port
80 display

The invention claimed is:

1. A method for detecting fluorescence by receiving fluorescence emitted by a measurement object irradiated with laser light and processing a fluorescent signal obtained at this time, the method comprising the steps of:
   irradiating the measurement object with laser light modulated at a predetermined frequency;
   receiving fluorescence emitted by the measurement object and outputting two or more pulsed fluorescent signals;
   setting reference timing in units of period corresponding to the frequency;
   acquiring a generation time to output of each of the pulsed fluorescent signals based on the reference timing;
   generating a cumulative fluorescent signal indicating a relationship between a generation frequency of the pulsed fluorescent signal and the generation time;
   determining, by using a signal corresponding to modulation of the laser light as a reference signal, a phase difference between the reference signal and the cumulative fluorescent signal; and
   determining, by using the phase difference, a fluorescence relaxation time of the fluorescence emitted by the measurement object.

2. The fluorescence detection method according to claim 1, wherein
   in the step of determining a phase difference, the phase difference is determined from a correlation value between the cumulative fluorescent signal and the reference signal.

3. The fluorescence detection method according to claim 1, wherein
   in the step of determining a phase difference, the phase difference is determined from a delay time of the cumulative fluorescent signal with respect to a modulation signal for modulating the laser light, the delay time being determined by fitting the cumulative fluorescent signal to a signal having a shape identical to that of the modulation signal.

4. The fluorescence detection method according to claim 1, wherein
   the signal corresponding to modulation of the laser light is acquired by receiving part of the laser light.

5. The fluorescence detection method according to claim 1, wherein
   the signal corresponding to modulation of the laser light is a modulation signal for modulating the laser light.

6. A device for detecting fluorescence by receiving fluorescence emitted by a measurement object irradiated with laser light and processing a fluorescent signal obtained at this time, the device comprising:
   a laser light source unit that irradiates a measurement object with laser light modulated at a predetermined frequency;
   a light-receiving unit that receives fluorescence emitted by the measurement object and outputs two or more pulsed fluorescent signals; and
   a processing unit that determines, by using the fluorescent signals output by the light-receiving unit by irradiation of the measurement object with the laser light, a fluorescence relaxation time of the fluorescence emitted by the measurement object,
   wherein the processing unit comprises:
   a reference timing setting unit that sets reference timing in units of period corresponding to the frequency;
   a pulse generation time acquisition unit that acquires a generation time to output of each of the pulsed fluorescent signals based on the reference timing;
   a cumulative fluorescent signal generation unit that generates a cumulative fluorescent signal indicating a relationship between a generation frequency of the pulsed fluorescent signal and the pulse generation time;
   a phase difference acquisition unit that determines, by using a signal corresponding to modulation of the laser light as a reference signal, a phase difference between the reference signal and the cumulative fluorescent signal; and
   a fluorescence relaxation time acquisition unit that determines, by using the phase difference determined by the phase difference acquisition unit, a fluorescence relaxation time of the fluorescence emitted by the measurement object.

7. The fluorescence detection device according to claim 6, wherein
   the phase difference acquisition unit determines the phase difference from a correlation value between the cumulative fluorescent signal and the reference signal.

8. The fluorescence detection device according to claim 6, wherein
   the phase difference acquisition unit determines the phase difference from a delay time of the cumulative fluorescent signal with respect to a modulation signal for modulating the laser light, the delay time being determined by fitting the cumulative fluorescent signal to a signal having a shape identical to that of the modulation signal.

9. A non-transitory computer readable medium storing a program for causing a computer to execute processing of two or more pulsed fluorescent signals obtained as a light-receiving signal of fluorescence emitted by a measurement object irradiated with laser light modulated at a predetermined frequency, the program comprising the steps of:
   causing a setting component of the computer to set reference timing in units of period corresponding to the frequency;
   causing a acquisition component of the computer to acquire a generation time to output of each of the pulsed fluorescent signals based on the reference timing;

causing a cumulative fluorescent signal generation component of the computer to generate a cumulative fluorescent signal indicating a relationship between a generation frequency of the pulsed fluorescent signal and the generation time;

causing a phase difference determination component of the computer to determine, by using a signal corresponding to modulation of the laser light as a reference signal, a phase difference between the reference signal and the cumulative fluorescent signal; and causing a fluorescence relaxation time determination component of the computer to determine, by using the phase difference, a fluorescence relaxation time of the fluorescence emitted by the measurement object.

10. The medium according to claim 9, wherein in the step of causing the phase difference determination component to determine a phase difference, the phase difference is determined from a correlation value between the cumulative fluorescent signal and the reference signal.

11. The medium according to claim 9, wherein in the step of causing the phase difference determination component to determine a phase difference, the phase difference is determined from at delay time of the cumulative fluorescent signal with respect to a modulation signal for modulating the laser light, the delay time being determined by fitting the cumulative fluorescent signal to a signal having a shape identical to that of the modulation signal.

* * * * *